United States Patent
Vath et al.

(10) Patent No.: US 12,086,228 B2
(45) Date of Patent: *Sep. 10, 2024

(54) LOGIN TOKEN MANAGEMENT

(71) Applicant: BOSTON SCIENTIFIC CARDIAC DIAGNOSTICS, INC., Rochester, MN (US)

(72) Inventors: Savy Vath, Rochester, MN (US); Gale G. McFarland, Rochester, MN (US); Kevin W. Kirkeby, Rochester, MN (US); Michael S. Butterbrodt, Stoughton, WI (US)

(73) Assignee: Boston Scientific Cardiac Diagnostics, Inc., Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/092,665

(22) Filed: Jan. 3, 2023

(65) Prior Publication Data

US 2023/0143584 A1  May 11, 2023

Related U.S. Application Data

(63) Continuation of application No. 16/445,409, filed on Jun. 19, 2019, now Pat. No. 11,550,891.

(51) Int. Cl.
| | |
|---|---|
| *G06F 21/33* | (2013.01) |
| *G06F 21/41* | (2013.01) |
| *G06F 21/60* | (2013.01) |
| *G06F 21/62* | (2013.01) |
| *G16H 10/60* | (2018.01) |

(52) U.S. Cl.
CPC .............. *G06F 21/33* (2013.01); *G06F 21/41* (2013.01); *G06F 21/602* (2013.01); *G06F 21/6245* (2013.01); *G06F 21/629* (2013.01); *G16H 10/60* (2018.01); *G06F 2221/2113* (2013.01); *G06F 2221/2137* (2013.01)

(58) Field of Classification Search
CPC ........................................... G06F 21/33
See application file for complete search history.

(56) References Cited

U.S. PATENT DOCUMENTS

| | | | |
|---|---|---|---|
| 6,243,816 B1 | 6/2001 | Fang et al. |
| 6,704,732 B1 | 3/2004 | Barclay |
| 7,042,988 B2 | 5/2006 | Juitt et al. |
| 7,284,271 B2 | 10/2007 | Lucovsky et al. |
| 7,546,633 B2 | 6/2009 | Garg et al. |
| 8,825,855 B2 | 9/2014 | Feng et al. |
| 11,550,891 B2 | 1/2023 | Vath et al. |
| 2003/0149714 A1 | 8/2003 | Casati et al. |
| 2017/0070517 A1 | 3/2017 | Bailey et al. |
| 2018/0069702 A1 | 3/2018 | Ayyadevara et al. |
| 2019/0243520 A1 | 8/2019 | Cao et al. |
| 2020/0401684 A1 | 12/2020 | Vath et al. |

*Primary Examiner* — Simon P Kanaan
(74) *Attorney, Agent, or Firm* — Faegre Drinker Biddle & Reath LLP

(57) ABSTRACT

Techniques for securing user data in a healthcare data management system are described. A client system receives a request to authenticate a user. A login token relating to an authenticated user is maintained at the client system. A role is selected for the user, and an authorization token relating to the selected role is maintained at the client system. A session for the user is initiated. This includes generating an encrypted session cookie relating to the user and the session, storing the encrypted session cookie at the client system, and periodically updating a timestamp for the session cookie.

20 Claims, 11 Drawing Sheets

# LOGIN TOKEN MANAGEMENT

CROSS REFERENCE TO RELATED APPLICATION

This application is a continuation application that claims priority to U.S. patent application Ser. No. 16/445,409, filed on Jun. 19, 2019, which is herein incorporated by reference in the entirety.

TECHNICAL FIELD

The present disclosure relates generally to data security in a computing environment, and more specifically, though not exclusively, to data security for healthcare data management systems by providing login token management for a multi-tenancy user session.

BACKGROUND

Healthcare data management systems allow for management, display, and storage of patient health data. For example, electronic sensors can be used to monitor patients, collect data relating to the patients' health, and evaluate potential health conditions. As one example, electronic signals related to the patients' health (e.g., electrocardiogram (ECG) signals) can be collected over time, evaluated, and used for treatment and care of patients. Other patient health data can similarly be collected, stored, and evaluated to assist in treating the patient.

As the amount of patient data becomes more readily available and the time demands on the medical caregiver continue to increase, there is a need to provide a highly scalable solution that allows care providers (and other authorized parties) access to the patient data. Moreover, as patient data is frequently sensitive information, information security is a top concern for any health care system. And more generally, outside of the medical space, the amount of data being collected and stored has continued to increase, along with the need to secure such data (particularly personal data). As such, there is a need for a highly scalable solution that ensures the security and integrity of data (e.g., collected medical data). Further, because parties accessing the patient data may not be sophisticated computer users, the solution should also be efficient and easy to use.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DESCRIPTION OF EXAMPLE EMBODIMENTS

Overview

Figure 1:
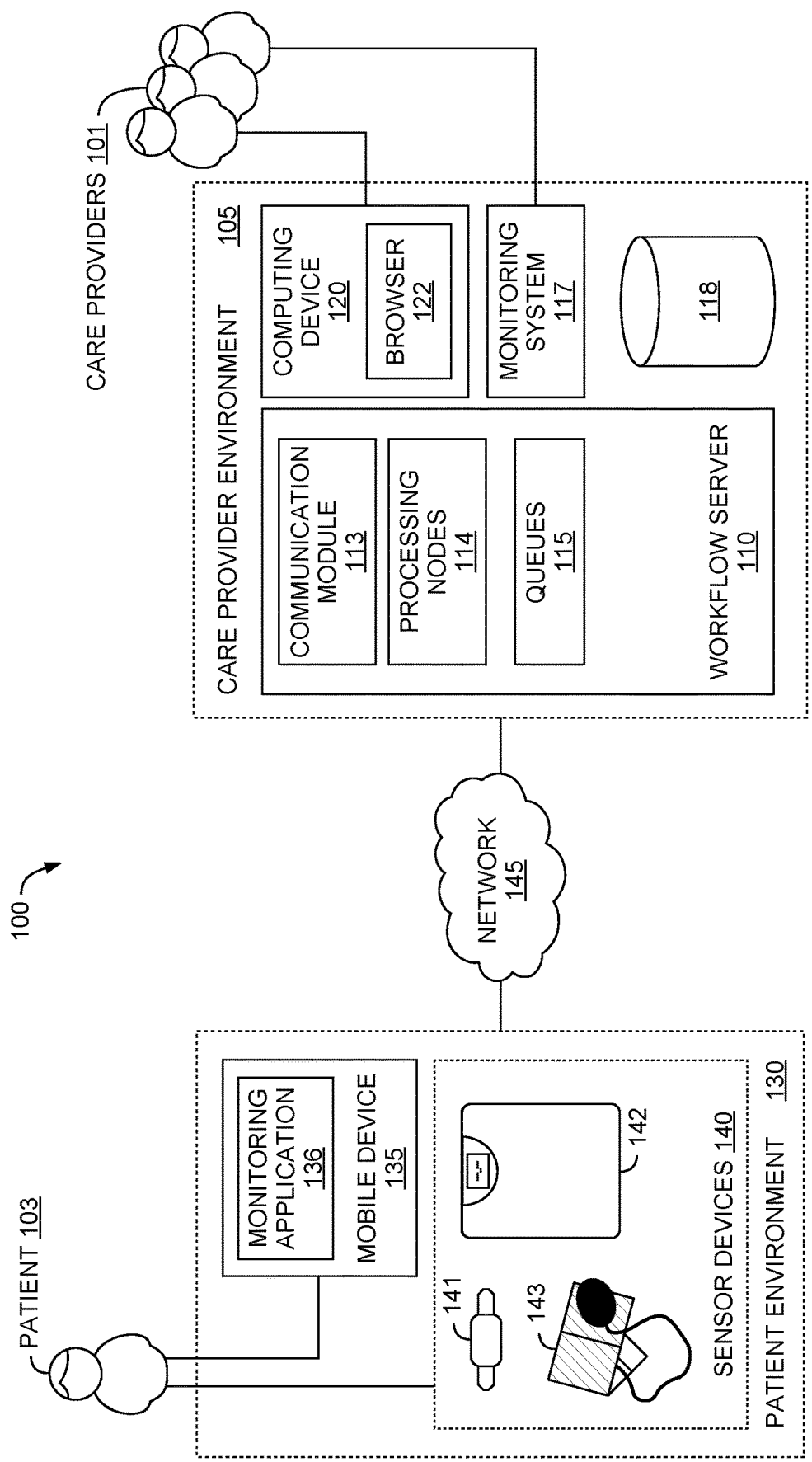
FIG. 1 illustrates an example computing environment, according to one embodiment described herein.

Embodiments described herein include a method of securing user data in a healthcare data management system. The method includes receiving, at a client system, a request to authenticate a user for the healthcare data management system. The user is associated with a plurality of applications relating to the healthcare data management system and a plurality of roles relating to the healthcare data management system. The method further includes authenticating the user, at the client system, for all applications of the plurality of application and all roles of the plurality of roles, and in response maintaining a login token relating to the authenticated user at the client system. The method further includes selecting a role from the plurality of roles, for the user, and in response maintaining an authorization token relating to the selected role at the client system. The method further includes initiating a session for the user in the healthcare data management system, including generating an encrypted session cookie relating to the user and the session, storing the encrypted session cookie at the client system, and periodically updating a timestamp for the session cookie.

Embodiments described herein further include a system. The system includes a processor and a memory containing computer program code that, when executed by the processor, performs an operation. The operation includes receiving, at a client system, a request to authenticate a user for a healthcare data management system. The user is associated with a plurality of applications relating to the healthcare data management system and a plurality of roles relating to the healthcare data management system. The operation further includes authenticating the user, at the client system, for all applications of the plurality of application and all roles of the plurality of roles, and in response maintaining a login token relating to the authenticated user at the client system. The operation further includes selecting a role from the plurality of roles, for the user, and in response maintaining an authorization token relating to the selected role at the client system. The operation further includes initiating a session for the user in the healthcare data management system, including generating an encrypted session cookie relating to the user and the session, storing the encrypted session cookie at the client system, and periodically updating a timestamp for the session cookie.

Embodiments described herein further include a non-transitory computer-readable medium containing computer program code that, when executed by operation of one or more computer processors, performs an operation. The operation includes receiving, at a client system, a request to authenticate a user for a healthcare data management system. The user is associated with a plurality of applications relating to the healthcare data management system and a plurality of roles relating to the healthcare data management system. The operation further includes authenticating the user, at the client system, for all applications of the plurality of application and all roles of the plurality of roles, and in response maintaining a login token relating to the authenticated user at the client system. The operation further includes selecting a role from the plurality of roles, for the user, and in response maintaining an authorization token relating to the selected role at the client system. The operation further includes initiating a session for the user in the healthcare data management system, including generating an encrypted session cookie relating to the user and the session, storing the encrypted session cookie at the client system, and periodically updating a timestamp for the session cookie.

Example Embodiments

Network aware devices provide a variety of opportunities for a care provider (e.g., a physician, nurse, technician, etc.) to improve patient care. An event manager can use the data provided by network aware devices or an "internet of things" (IoT) device to identify health events that range from identifying critical health care issues such as cardiac or respiratory emergencies to maintenance events where the network aware device fails, e.g., because a battery is low or a wire is disconnected. To process health related events, an event manager may process events using a collection of defined paths. Further, a patient care environment may collect, report, and display health related events and collected health data.

Various users may wish to view and access this data using a healthcare data management system. For example, patients, care providers, healthcare administrators, information technology administrators, and others, may all wish to view patient data. To safeguard patient privacy, and data security, it is important to ensure that a user is authenticated, and authorized, before allowing the user to view requested data. But many care provider environments allow for multi-tenancy, meaning one user can have multiple different roles at different institutions, and can use multiple different applications to access and manage patient data.

For example, a care provider (e.g., a doctor) may be authorized to access some patient data at a given institution (e.g., a given hospital). But the care provider may have multiple roles at the institution (e.g., primary care provider, secondary care provider, and observer). The care provider's data access privileges can depend on the selected role. For example, as a primary care provider the care provider may be authorized to access and modify all healthcare related data for a patient, while as an observer the care provider may be authorized to access only some data and may not be authorized to modify any data. Further, the care provider's potential roles can vary between institutions (e.g., the care provider may only be an observer at some institutions, or may have a different role).

And as another complication, a user may have access to multiple different applications. For example, one application may allow modification of patient biographical data, while another application may facilitate diagnosis and treatment of a particular medical condition (e.g., a cardiac condition). Thus, a given user may have access to multiple different applications, roles, and institutions. In prior systems, local data is often maintained using the Local Storage features of web browsers. But this is not suitable for a multi-tenancy system, in which a user can have access to multiple different applications, roles, and institutions.

Techniques disclosed herein relate to providing user-friendly, yet secure, solutions to these problems in healthcare data management systems. For example, a shared login framework can be used to authenticate a user (e.g., using a password, fingerprint, biometric scanner, etc.) across multiple applications, institutions, and roles. An encrypted login token can be stored on the user's local computer and used to memorialize and manage this authentication across the various applications, institutions, and roles. Further, a shared application and role selection framework can be used to determine that a user is authorized to access and manage particular dat. An encrypted authorization token can be stored on the user's local computer and used to memorialize and manage this authorization across the various applications, institutions, and roles. And one or more encrypted session cookies can be stored locally and used to manage a user's session, across the various applications, institutions, and roles. Managing these frameworks at the client level, rather than requiring interaction with a server system, provides for a more secure and user friendly system.

Patient Care Environment

FIG. 1 illustrates an example computing environment 100, according to one embodiment described herein. As shown, the computing environment 100 may include a care provider environment 105 and a patient environment 130, each connected to one another via a network 145. The care provider environment 105 and the patient environment 130 allow a care provider 101 (e.g., a technician, nurse, physician, etc.) to monitor biometric data generated by the patient 103.

The care provider environment 105 includes a workflow server 110, a computing device 120, monitoring system 117 and data repository 118. Each of the workflow server 110, the computing device 120, and the monitoring system 117 may be a physical computing system or a virtual computer instance (e.g., executing in a cloud computing platform). A care provider 101 may use the computing device 120 to access (e.g., via a browser 122, a native application on device 120, etc.) a user interface (UI) hosted by the monitoring system 117.

Of note, although shown as a single entity, the data repository 118 can represent multiple, separate data stores (e.g., relational databases). Moreover, these data stores can span multiple computing nodes. To this end, the separate data stores could be made to function as a single data store (e.g., through data replication techniques and through the use of load balancers). As such, the data repository 118 is representative of any sort of data store on any number of computing systems, consistent with the functionality described herein.

Additionally, although not shown, the data repository 118 may store data from and/or service requests from various other entities, such as third party applications, partners and affiliates, electronic medical record systems, external monitoring devices and products, analytics engines, data consolidator applications and so on. More generally, it is contemplated that the data repository 118 and, more generally, other elements within the care provider environment 105, can interact with any number of different data originators and receipts, consistent with the functionality described herein. As such, the computing environment 100 is provided merely for illustrative purposes only and without limitation.

The workflow server 110 includes applications and data executed to identify and handle health events corresponding to the patient 103. As shown, workflow server 110 includes a communication module 113, processing nodes 114, and queues 115. In one embodiment, the processing nodes 114 are software code or applications that perform a predetermined task or action on received data (e.g., health events). The workflow server 110 evaluates data received from the patient environment 130 using a set of interconnected processing nodes 114 and the queues 115 which form a workflow. As the biometric data or health events are received from the patient environment 130, the workflow may classify (or reclassify) the data to identify a type of the health event—e.g., presentation or notification to patient/care provider, suppression, classification, aggregation, computation, prioritization/triage, and the like. For example, different types of data received from the patient environment 130 may trigger different types of health events—e.g., an irregular heartbeat may trigger a cardiac event, while a signal indicated an electrode has become detached triggers a maintenance event. In one embodiment, at least one sensor device 140 within the patient environment 130 or a monitoring application 136 installed as part of a mobile device 135 within the patient environment 130 may have performed an initial classification of the data or health events. Nonetheless, the workflow server 110 may evaluate the biometric data (or maintenance data) to confirm that this initial classification was correct.

Each type of health event may take a different path through the workflow. That is, different health events may traverse the processing nodes 114 and the queues 115 using different paths. For example, a cardiac event may be evaluated using different processing nodes 114 in the server 110 than a maintenance event. Furthermore, paths through the workflow for the same health event may differ based on a variety of factors such as the severity of the health event, age of the patient 103, other symptoms exhibited by the patient 103, medication taken by the patient 103, and the like. For example, a high priority cardiac event may skip one or more of the processing nodes 114 or the queues 115 and be immediately displayed to the care provider 101 using the monitoring system 117.

The communication module 113 permits the workflow server 110 to receive the data from the patient environment 130 and transmit data to the care providers 101. The communication module 113 may receive data from the at least one sensor device 140 which is used to identify a health event and a corresponding path through interconnected ones of the processing nodes 114 and the queues 115. The communication module 113 helps the care providers 101 complete the workflow by use of the monitoring system 117 and the computing device 120. Moreover, in addition to receiving the data from the patient environment 130, the communication module 113 may enable the workflow server 110 to transmit requests or instructions to the patient environment 130 such as asking the patient 103 if she has any symptoms or instructing the patient 103 to reattach a disconnected electrode (not shown) of the at least one sensor device 140.

In one embodiment, a path used by a health event to traverse the workflow server 110 may include processing nodes 114 that process the health event without user intervention as well as the processing nodes 114 that require input from the care providers 101. For example, one of the processing nodes 114 may filter or screen a health event to determine what queue to place the event, compare the event to one or more rules to determine an action to perform, or store the event. Alternatively, others of the processing nodes 114 may require the care provider 101 to perform an action or provide instructions. For example, the monitoring system 117 may generate a user interface (UI) for a health event which is then displayed to the care provider 101 by the browser 122. Once the care provider 101 performs an action (e.g., confirms the classification of the event or agrees with an action suggested by the workflow server 110), the remaining operations of the workflow are performed—e.g., send a notification to the patient 103, log the event in the history of the patient 103, route the event to a different one of the care providers 101, reclassify the health event (if the care provider 101 indicated the initial classification was incorrect), or prioritize or triage the health event.

With continued reference to FIG. 1, the patient environment 130 includes the mobile device 135 and the at least one sensor device 140. The mobile device 135 includes the monitoring application 136 which permits communication between the at least one sensor device 140 and the care provider environment 105 via the network 145. The monitoring application 136 may configure the at least one sensor device 140 (e.g., IoT devices) to monitor biometric data of the one or more patient 103 as specified by a care plan. For example, the monitoring application 136 could configure logic on a heart rate monitoring device worn by the patient to monitor the patient's heart rate. In turn, the monitoring application 136 can send the heart rate data to the workflow server 110 which determines if a heath event is triggered, and if so, executes a workflow to process the event as described above. In another embodiment, the heart rate monitoring device, upon detecting that a threshold condition has been satisfied, could generate and transmit a health event to the mobile device 135, which in turn transmits the health event to the workflow server 110 for processing. However, in other embodiments, some of the tasks performed by the workflow server 110 may be performed by the mobile device 135. That is, the workflow may include tasks performed by the mobile device 135 or the at least one sensor device 140 as well as tasks performed by the workflow server 110.

In one embodiment, the monitoring application 136 receives environmental data from the at least one sensor device 140. Generally, the environmental data informs the monitoring application 136 of environmental conditions in an area proximate to the at least one sensor device 140 and the user—e.g., a room in which the user is located. For example, the at least one sensor device 140 may detect an air quality or pollen count for the patient 103 having a respiratory ailment. In another example, the at least one sensor device 140 may track the user's movements or actions in an environment such as how many times at night the patient 103 goes to the bathroom or if the patient 103 is tossing and turning at night. This environmental data can then be used by the monitoring application 136 by itself, or in combination with the biometric data, to trigger health events which are processed by the workflow server 110.

In one embodiment, the monitoring application 136 may use an output device (e.g., a display or audio system) on the mobile device 135 to provide information to the patient 103. For example, when executing a workflow, one of the processing nodes 114 may ask the patient 103 if she is experiencing any symptoms. To obtain feedback from the patient 103, the monitoring application 136 may display a user interface (UI) on the mobile device 135 which permits the patient 103 to list symptoms. Moreover, the monitoring application 136 may also display general information related to a care plan or the at least one sensor device 140 such as the patient's heart rate or weight, status of the at least one sensor device 140, etc.

In one embodiment, the at least one sensor device 140 interacts with the monitoring application 136 and assists the patient 103 in reporting patient vitals and other information to the care provider environment 105. As shown, the at least one sensor device 140 may include a body sensor 141, a weighing scale 142, and a blood pressure cuff 143. Each of the at least one sensor device 140 may capture different vitals of the patient 103. For example, when applied to a body of patient 103, the body sensor 141 captures biometric data (e.g., heart rate, ECG data, etc.) in real-time. In addition, each of the at least one sensor device 140 may be configured to transmit body-related metrics electronically to the monitoring application 136 on the mobile device 135. In turn, the monitoring application 136 sends the captured metrics to the workflow server 110 which can be used to trigger health events which are processed using the processing nodes 114 and the queues 115.

In one embodiment, upon detecting an observation threshold has been reached, the at least one sensor device 140 performs an initial classification of the health event. In a particular embodiment, the mobile device 135 is configured to perform the initial classification of the health event. For example, the body sensor 141, upon detecting that ECG data collected from the patient 103 indicates an erratic heart behavior, could classify the health event as a cardiac event. This initial classification of the health event, along with the relevant ECG data (e.g., ECG data including a predetermined length of time before and after the event), could be transmitted to the mobile device 135 (e.g., over a Bluetooth® communications link) and the monitoring application 136 subsequently forwards the ECG data and the health event data on to the workflow server 110 over the network 145 (e.g., the Internet). Alternatively, instead of classifying the data, the monitoring application 136 may forward the raw, unprocessed sensor data to the workflow server 110 which uses one of the processing nodes 114 to identify and classify health events which are then processed in the workflow server 110.

Figure 2:
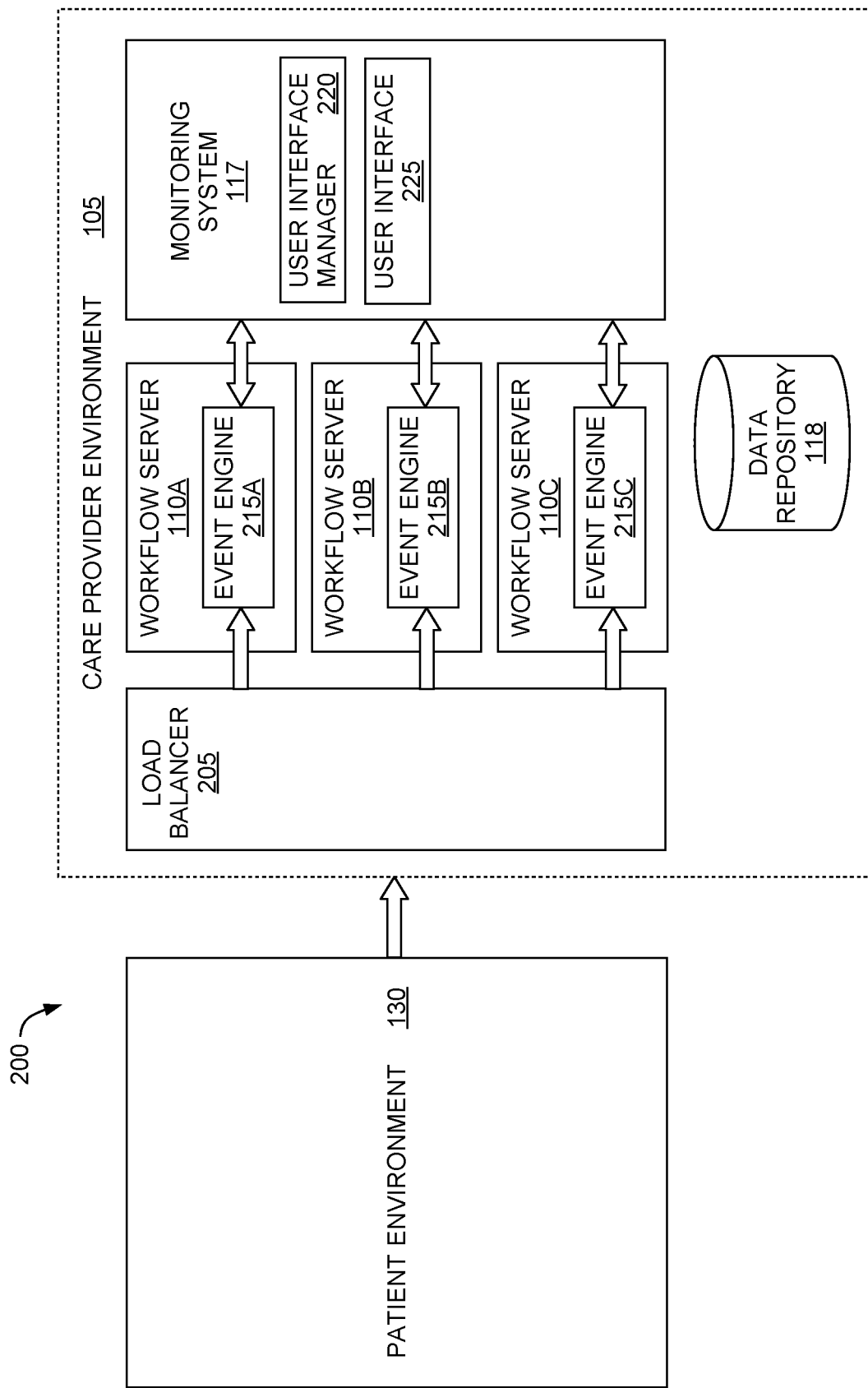
FIG. 2 illustrates a parallel processing computing environment, according to one embodiment described herein.

FIG. 2 illustrates a parallel processing computing environment 200, according to one embodiment described herein. As shown, the patient environment 130 transmits biometric data and/or health events to the care provider environment 105 which includes a load balancer 205. The workflow servers 110A-110C each include a respective one of the event engines 215A-215C. Although not shown, each of the event engines 215A-215C includes a plurality of interconnected processing nodes and queues that form a workflow for processing health events as discussed above. In one embodiment, the event engines 215A-215C each includes the same processing nodes and queues arranged in the same manner such that any one of the event engines 215A-215C can process the different health events generated by the at least one sensor device 140—i.e., any one of the event engines 215A-215C can process a cardiac event, respiratory event, maintenance event, etc. Based on current workload, the load balancer 205 transmits received data or heath events to one of the workflow servers 110A-110C for processing. For example, the load balancer 205 may assign the received health events in a round robin manner or by monitoring each respective central processing unit (CPU) or memory usage of the workflow servers 110A-110C.

Alternatively, the event engines 215A-215C may have different processing nodes and queues (or a different arrangement of the nodes and queues) such that the event engines 215A-215C are configured to process different event types. For example, the event engines 215A, 215B may have workflows that process cardiac events (and have the same processing nodes and queues), while the workflow in the event engine 215C processes respiratory events. The load balancer 205 may determine which of the event engines 215A-215C should receive the health event using the initial classification provided by the patient environment 130 or based on which of the at least one sensor device 140 measured the biometric data.

Regardless whether the event engines 215A-215C have the same arrangement or different arrangements, compute resources can easily be adjusted in response to varying workloads. For example, if additional sensor devices (e.g., sensor devices 140) are added to the patient environment 130, a system administrator can add additional ones of the workflow servers 110A-110C to process an increased number of received health events. The reverse is also true. If the number of health events decreases, the administrator may remove one or more of the workflow servers 110A-110C. For example, if the event engines 215A, 215B both process cardiac events but the number of cardiac events has decreased, the system administrator may remove one of the workflow servers 110A, 110B. As another example, a load balancer component could monitor the usage of computational resources by the workflow servers 110A-110C and could scale the number of servers up or down, based on the computational resource usage.

With continued reference to FIG. 2, the monitoring system 117 includes a user interface manager 220 (UI manager) and a user interface 225 (UI). As discussed above, the processing nodes 114 may require input from the care provider 101 (FIG. 1) in order to route the health events through the event engines 215A-215C. To do so, the event engines 215A-215C transmit requests to the UI manager 220 which generates the UI 225 which can be displayed to the care provider 101. For example, the UI manager 220 may generate the UI 225 that includes an electrocardiogram (ECG) chart corresponding to a cardiac event. Further, the UI 225 may include I/O features (e.g., buttons or pull down menus) that the care provider can use to provide input or instructions to one of the event engines 215A-215C. For example, the care provider may instruct the one of the event engines 215A-215C to store the cardiac event in the data repository 118, send the cardiac event to one of the queues 115 (FIG. 1) that is monitored by another care provider (e.g., to get a second opinion), or forward the cardiac event to the care provider 101 of the patient 103. Thus, the monitoring system 117 permits the workflow servers 110 to output information to the care provider 101 as well as receive instructions from the care provider 101.

The event engines 215A-215C may store data in and retrieve data from the data repository 118. For example, the event engines 215 may maintain a patient history by storing all the received health events (or selected health events) derived based on monitoring a patient's vitals in the repository 118. Further, the event engines 215A-215C may use the data stored in the data repository 118 to process the health events. For example, if one of the event engines 215A-215C receives biometric data indicating the current weight of the patient 103, then the one of the event engines 215A-215C can retrieve past weight measurements for the patient 103 from the data repository 118 and derive a trend graph detailing how the weight of the patient 103 has changed over time. For instance, the patient's current weight may not be enough to trigger a health event, but the patient's derived weight change over a period of time may trigger a health event. As discussed below, these derived trends may be used to generate a derived observation (or other event(s)).

In one embodiment, the event engines 215A-215C prioritize health events, which, in turn, determines how quickly the health events are processed by the workflows in the event engines 215A-215C or what processing nodes and queues are used to process the health events. As discussed above, the health events may be prioritized based on a severity of the health event, the type of the health event, a characteristic of the patient 103 whose biometric data generated the health event, and the like. Additionally, the health events could be prioritized based on additional criteria, such as an institutional policy, a care plan-level policy, a patient-level policy, another policy or some combination of the above.

Figure 3:
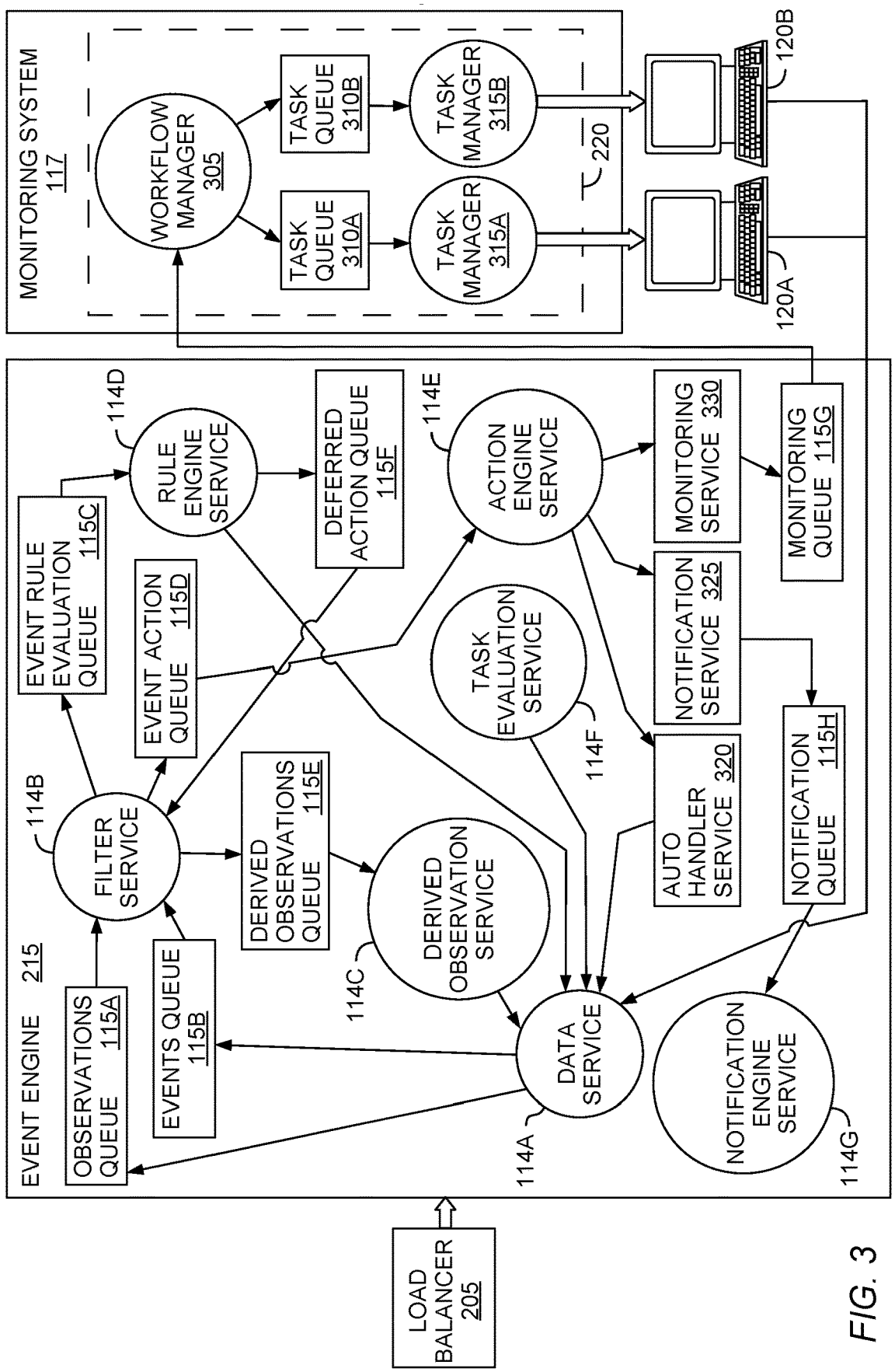
FIG. 3 illustrates an event engine that includes a workflow for processing health events, according to one embodiment described herein.

FIG. 3 illustrates an event engine 215 that includes a workflow for processing health events, according to one embodiment described herein. As described above, a health event or biometric data received from the sensors is forwarded from the load balancer 205 to the event engine 215. Specifically, a data service node 114A in the workflow receives the forwarded information from the load balancer 205. If the load balancer 205 forwards a health event, the data service node 114A classifies the health event based on type (e.g., a cardiac, respiratory, or maintenance event). In some cases, the health event was classified before being received by the data service node 114A. Nonetheless, the data service node 114A may review the data associated with the health event such as ECG data, breathing rate, blood pressure, etc. using more compute intensive techniques to determine whether the initial classification was correct. In another example, the data service node 114A may provide a more detailed classification of the health event than the initial classification. For example, the sensor device may have generated the health event because it detected an irregular heartbeat. However, the data service node 114A may evaluate the heartbeat and classify the health event as a specific cardiac health event—e.g., a ventricular trigeminy event or an atrioventricular block event. The data service node 114A may save the classification of the health event which is used by downstream nodes and queues to process the health event.

Instead of receiving a health event, the data service node 114A may receive raw data or observations from the patient environment. That is, the raw data or observations may not have been evaluated by a sensor device worn by the patient to determine if this data triggers a health event. For example, observation data from a sensor includes blood pressure measurements, weight measurements, ECG data, and the like. As discussed below, the event engine 215 evaluates these observations and can trigger health events which are then processed in the engine 215.

The data service node 114A forwards the observations to the observation queue 115A and the health events to the events queue 115B. A filter node 114B pulls the observations and health events stored in the queues 115A and 115B. This node 114B serves as a gatekeeper that determines where the health events and observations are routed for further processing. When evaluating observations, the filter node 114B may determine whether to ignore (i.e., drop) the observations or forward the observations to a derived observation queue 115E. For example, observations such as low battery signals, start signals indicating a sensor device has started collecting biometric data, or stop signals indicating a sensor device has stopped may be ignored by the filter service node 114B. In contrast, the node 114B may forward observations such as weight measurements, blood pressure measurements, ECG data, and the like to the derived observation queue 115E. In this manner, the filter service node 114B screens the incoming observations to determine whether they should be processed further such as checking for triggering health events.

Observations forwarded by the filter service node 114B are then processed by a derived observation service node 114C. This node 114C uses received observations in conjunction with previously received observations to create new observations or to generate a new health event. Stated differently, the derived observation service 114C may aggregate previously received observations with the currently received observations to compute statistics, trends, trigger health events, and the like. Although not shown, node 114C may be communicatively coupled to the data repository which stores past observations. For example, if the currently received observation is a weight measurement, the derived observation service node 114C may evaluate this measurement with previous weight measurements to determine a weight change for the patient over a defined period of time. This weight change may trigger a health event which is then forwarded to the data service node 114A for further processing. Even if a health event is not triggered, the derived observation service node 114C may store a derived observation (e.g., a weight change, average blood pressure, heart rate trends, etc.) in the data repository so that this data is available when further observations for the patient are received by the event engine 215 (or other event engines 215).

In one embodiment, health events may be processed by the derived observation service node 114C. For example, a sensor device may trigger a health event upon determining a patient's average blood pressure for a day exceeds a threshold. The filter service node 114B may forward this health event to the derived observation service node 114C which then may use past blood pressure measurements for that patient to derive a weekly or monthly average blood pressure for the patient, or a blood pressure trend graph. Based on this derived observation, the node 114C may generate a new health event or decide to drop the health event if the derived observation does not satisfy a corresponding condition.

Further, filter service node 114B also includes logic for determining whether received health events should be dropped, forwarded to an event action queue 115D, or forwarded to the event rule evaluation queue 115C. For example, a system administrator may determine that some health events are not relevant for certain patients. The logic in the filter service node 114B may identify and drop these health events to prevent them from propagating through the rest of the event engine 215. For instance, a patient may have a heart murmur that constantly results in a sensor device triggering a health event. Rather than continually processing these health events, a care provider can instruct the filter service node 114B to screen out (or suppress) these health events from the patient.

If a received health event has a corresponding action or actions, the filter service nodes 114B forwards the health event to the event action queue 115D. However, if the action for a health event has not yet been identified, the filter service node 114B forwards the health event to the event rule evaluation queue 115C. A rule engine service node 114D pulls the health events from the queue 115C and evaluates the health event using one or more rules. Example rules include determining whether daily weight change and average blood pressure exceed respective thresholds. Based on this evaluation, the node 114D may determine what action the event engine 215 should perform—e.g., suppress/ignore the event, auto handle the event, display the event to a care provider, or delay processing the event. Once the action is determined, the rule engine service node 114D generates and forwards a new health event that includes the corresponding action to the data service node 114A. Now that the corresponding action is known, once the new health event reaches the filter service node 114B, it forwards the event to the event action queue 115D rather than the event rule evaluation queue 115D.

The rule engine service node 114D may delay processing the health event by forwarding the event to a deferred action queue 115F. The node 114D may do so when there is not enough available computing power to perform the rule evaluation or if the rule evaluation has not yet completed. That is, if all of the rules have not yet been evaluated and further evaluation is required before triggering the event action, then the event may be placed in queue 115F. For example, the rule may trigger a cardiac event but the system must first check to determine if that event is suppressed for the patient before taking the corresponding action. As shown, the health events stored in the deferred action queue 115F are then retrieved by the filter service node 1148 and can be reintroduced into the event rule valuation queue 115C at a later time—i.e., when all the rules have been evaluated.

Once a corresponding action for a health event is known and the health event is stored in the event action queue 115D, an action engine service node 114E routes the health event to the appropriate action service—i.e., auto handler service 320, notification service 325, or monitoring service 330. The auto handler service 320 may perform actions that do not require supervision or input by a care provider—e.g., stores the health event in the data repository. As another example, the auto handler service 320 may assign a priority or severity to the health event before the event is reintroduced into the workflow with the new priority. The auto handler service 320 may also generate a new health event when, for example, a health event shows a cardiac event but the data quality is low. In response, the service 320 may introduce a maintenance event for checking the sensor connection/electrodes.

The event engine 215 uses notification service 325 to send information to the patient, a care giver, car provider, or device regarding the health event. The notification service 325 may include different communication channels or techniques for communicating with the patient such as email, chat, SMS messages, etc. Although FIG. 3 illustrates only one notification queue 115H and notification engine service node 114G for handling requests, the event engine 215 may have different queues and notification nodes for the different communication techniques. For example, if a maintenance event is triggered when an electrode is unplugged from a sensor device, the notification service 325 may transmit an email to the patient's mobile device instructing the patient to plug in the electrode. Alternatively, if a respiratory event is triggered because of an elevated breathing rate, the notification service may send an SMS message to the patient asking her if she is currently performing a physical activity.

The monitoring service 330 communicatively couples the event engine 215 to the monitoring system 117. When input from a care provider regarding a health event is desired, the monitoring service 330 forwards the health event to a monitoring queue 115G. The UI manager 220 in the monitoring system 117 includes a workflow manager node 305 that pulls health events from the monitoring queue 115G and assigns them to either task queue 310A or 310B. The UI manager 220 also includes task manager nodes 315A and 315B which generate UIs for the health events. These UIs are then displayed to care providers via the computing devices 120A and 120B. Further, the task manager nodes 315 may place the biometric or maintenance data associated with the health events in the UIs. For example, a UI for a cardiac event may display an ECG graph and a baseline chart, while a UI for respiratory event displays a breathing rate and oxygen levels in the blood. In this manner, the UI manager 220 can generate a customized UI for the different health events.

The computing devices 120 may transmit information to the data service node 114A of the event engine 215 which can be used to generate new health events or update current health events. For example, the care provider may instruct the event engine 215 to take a certain action such as forwarding the health event to a different care provider to get a second opinion, reclassifying the health event, suppressing or ignoring the health event, notifying a health care provider, and the like. Based on the care provider's input, the event engine 215 again routes the health event through the nodes 114 and queues 115.

The event engine 215 also includes a task evaluation service node 114F. Unlike the other nodes and queues in event engine 215 which process or store observation data or health events received from the patient environment, the task evaluation service node 114F determines whether to trigger a health event based on a care protocol or care plan. In one embodiment, the node 114F triggers a health event when the patient does not follow the care protocol or plan. For example, the care protocol may ask that the patient wear a sensor device for certain amount of time during the day or take weight measurements each day. By monitoring the observation and health events received by the event engine 215, the task evaluation service node 114F determines whether the patient has complied with the care protocol. If not, the task evaluation service node 114F triggers a health event with a corresponding action for the event engine 215 to perform such as sending a notification to the patient using notification service 325 or informing a care provider using the monitoring service 330.

Login Token Management

Figure 4:
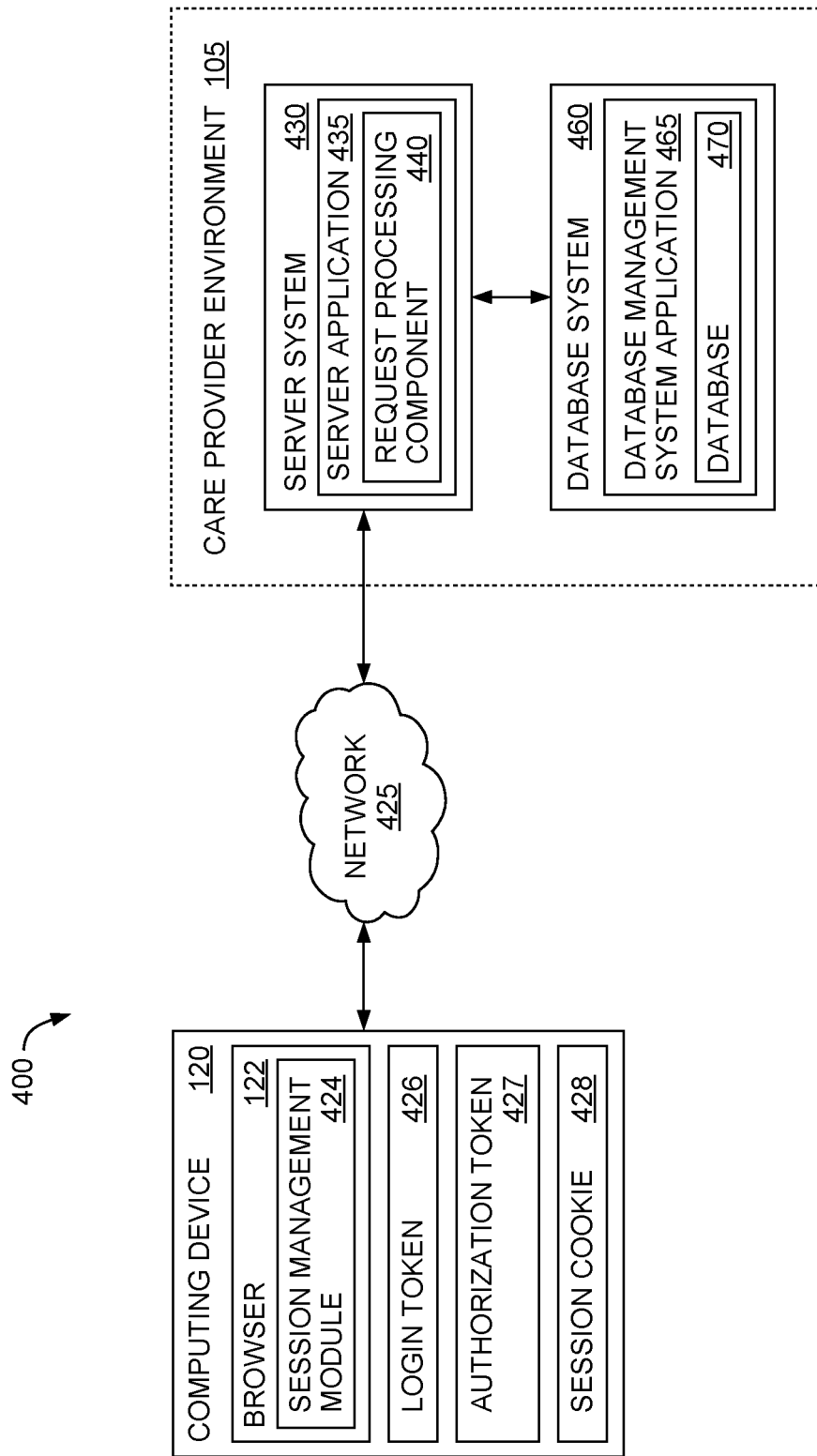
FIG. 4 is a block diagram illustrating a system configured with a login token management component, according to one embodiment described herein.

FIG. 4 is a block diagram illustrating a system (e.g., a healthcare data management system) configured with a login token management component, according to one embodiment described herein. As discussed below, this architecture facilitates a shared login framework and shared application selection and role selection frameworks, through management at the client using tokens and cookies. As shown, the system 400 includes a computing device 120 and the care provider environment 105, interconnected via a network 425. In an embodiment, the computing device 120 serves as a client system. The computing device 120 includes a browser 122 (e.g., a web browser). In an embodiment, the browser 122 accesses a page including a session management module 424. Alternatively, the browser 122 could be a stand-alone application (e.g., a rich or fat client), or could access a locally stored application (e.g., not a web page) including a session management module 424. Generally, the computing device represents any computer system capable of hosting the browser 122 (e.g., a computer system within a monitoring center, a physician's computer system, a patient's computer system or mobile device, etc.).

The computing device 120 (e.g., the client system) further includes a login token 426. As discussed further with regard to FIGS. 5 and 6, below, in an embodiment the login token 426 is a locally stored encrypted token used to manage authentication of a user. The computing device 120 further includes an authorization token 427. As discussed further with regard to FIGS. 5 and 6, below, in an embodiment the authorization token 427 is a locally stored encrypted token used to manage authorization of a user across different roles, institutions, and applications. The computing device 120 further includes a session cookie 428. As discussed further with regard to FIGS. 5 and 6, below, in an embodiment the session cookie 428 is a locally stored encrypted cookie used to manage a user's session.

Although a single login token 426, authorization token 427, and session cookie 428 is shown, it is contemplated that any number of login tokens, authorization tokens, and session cookies can reside on (or be accessible by) the computing device 120. Moreover, while the login token 426, authorization token 427, and session cookie 428 are shown as residing within the computing device 120, more generally the login token 426, authorization token 427, and session cookie 428 can reside on any storage device that is accessible by the computing device 120 (e.g., a flash memory device communicatively connected to the communication device 120).

The care provider environment 105 includes a server system 430 and a database system 460. The server system 430 includes a server application 435. The server application 435 includes a request processing component 440. The database system 460 includes a database management system (DBMS) application 465, which in turn includes a database 470. Generally, the DBMS application 465 manages access to the database 470 (e.g., processing queries against the database 470).

Figure 5:
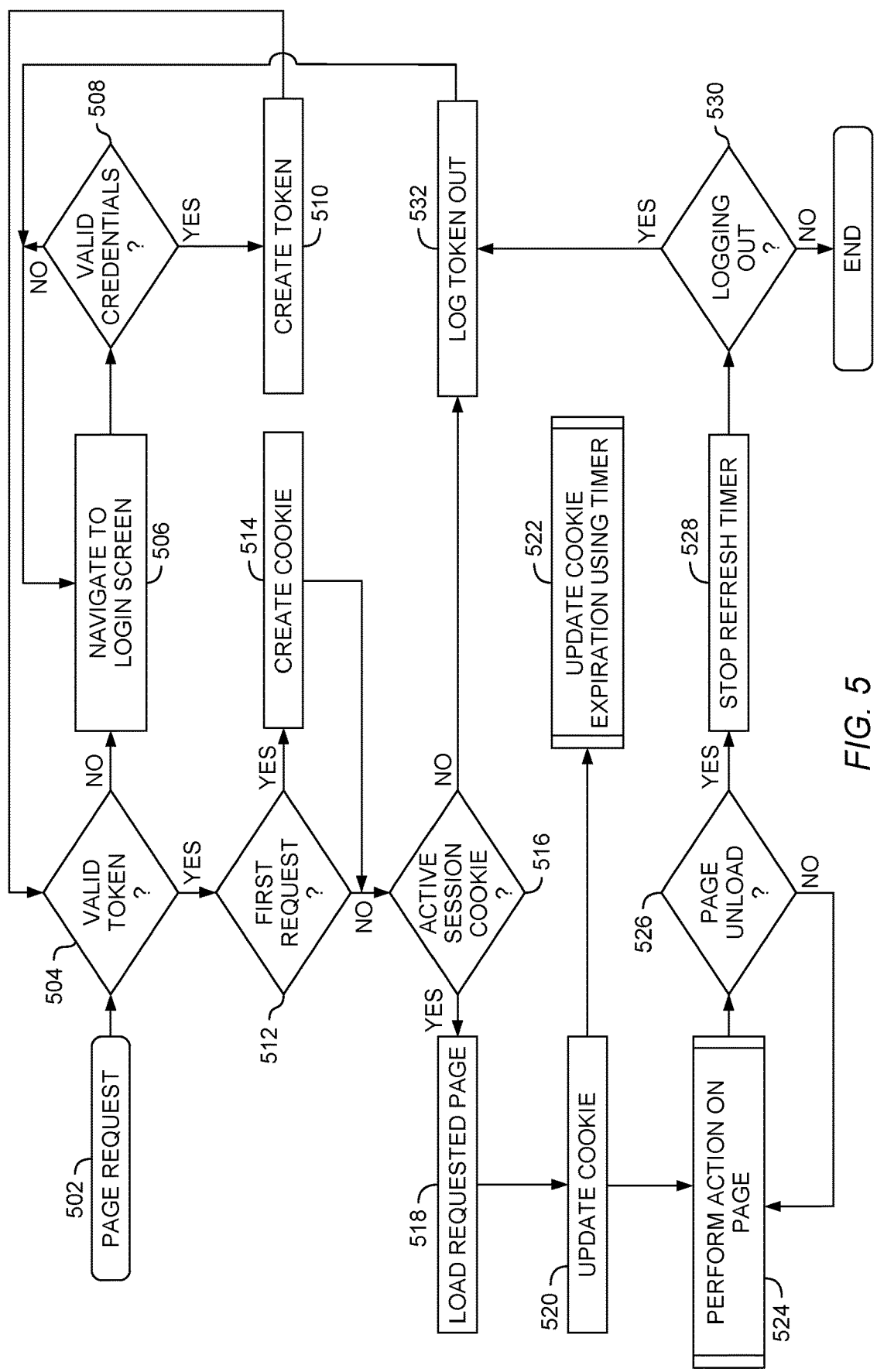
FIG. 5 is a flowchart illustrating client-side login token management, according to one embodiment described herein.

FIG. 5 is a flowchart illustrating client-side login token management, according to one embodiment described herein. At block 502, a client browser (e.g., the browser 122 illustrated in FIG. 4) receives a request to navigate to a page including an application (e.g., an application related to managing health data, as described above). At block 504, a session management module for the application (e.g., the session management module 424 illustrated in FIG. 4) checks whether the client system (e.g., the computing device 120 illustrated in FIG. 4) has a valid login token (e.g., the login token 426 illustrated in FIG. 4). In an embodiment, the session management module can store a login token locally (e.g., on the computing device 120 illustrated in FIG. 4) to memorialize previous authentication of the user. If the session management module determines that the client system does not have a valid login token, the flow proceeds to block 506.

At block 506, the session management module navigates the browser to a login screen to authenticate the user. In an embodiment, as discussed above, a single login screen can be used to authenticate a user for a variety of applications, roles, and institutions. At block 508, the session management module receives credentials from the user (e.g., a username and password, a fingerprint or other biometric scan, multi-factor authentication credentials, or other suitable credentials) and determines whether the credentials are valid. In an embodiment, this is done through communication with a care provider environment (e.g., the care provider environment 105 illustrated in FIG. 4) using a network (e.g., the network 405 illustrated in FIG. 4) and using known authentication techniques.

At block 510, if the session management module has determined that the credentials are valid, it creates a login token and stores it locally on the computing device. The session management module then returns to block 504 and checks for a valid login token. Returning to block 508, if the session management module determines that the credentials are not valid, it returns to block 506 and the login screen. In an embodiment, the session management module displays an error message and asks the user to re-enter his or her credentials on the login screen.

Returning to block 504, if the session management module determines that the computing device has a valid token, the flow proceeds to block 512. At block 512, the session management module determines whether the navigation request (e.g., received by the browser at block 502) is the first request since the user was authenticated. If so, the session management module proceeds to block 514 and creates a session cookie on the client system (e.g., the session cookie 428 illustrated in FIG. 4). In an embodiment, the session cookie is initialized with a timeout timer. For example, this timer can be set to a predetermined value (e.g., 30 seconds). As another example, the user can enter a timeout value, or the timeout value can be retrieved from local or remote storage.

The session management module then proceeds to block 516. At block 516, the session management module determines whether the client system has an active session cookie. If not, the session management module proceeds to block 532. At block 532, the session management module logs out the login token (e.g., deletes the token or marks it as invalid) and returns to block 506, where the user re-enters his or her credentials. In an embodiment, the session management module can maintain one session cookie for all active browser windows and tabs. Alternatively, the session management module can maintain multiple session cookies (e.g., a session cookie corresponding to each active browser window or tab).

Returning to block 516, if the session management module finds an active session cookie, proceeds to block 518. At block 518, the browser loads the requested page. At block 520, the session management module updates the session cookie. In an embodiment, the session management module resets the timer using the session cookie. The session management module also proceeds to block 522.

At block 522, the session management module periodically updates the active session cookie expiration using a timer. In an embodiment, the session cookie includes an expiration time (e.g., 30 seconds). The session management module refreshes this session cookie expiration timestamp at set intervals (e.g., every two seconds) using a timer. In one embodiment, this interval is predetermined. In another embodiment, this interval is configured by a user or retrieved from local or remote storage. For example, at block 522 the session management module uses a timer to reset the session cookie expiration timestamp every 2 seconds.

In an embodiment, the session cookie expiration is used to manage the session duration for the user. For example, the session management module can track activity using the session cookie. If the session cookie has not been updated for a defined duration (e.g., 20 minutes), the session management module can force the last active window to become active again, and can show a user interface message to the user indicating that the window corresponding to the session cookie is still open and logged in. This can help ensure that a user does not inadvertently leave a window logged in for longer than intended, potentially allowing an unauthorized user to access the logged in window and creating a security issue. In an embodiment, the duration can be pre-set on the local system, can be retrieved from a remote system, or can be configured by a local administrator or user.

Further, the session cookie expiration, along with a suitable token (e.g., the login token 426 and authorization token 427 illustrated in FIG. 4) can be used to allow a user to re-establish a session after inadvertently closing a browser window or tab. For example, if a user attempts to login, the session management module can identify the active (and not-expired) session using the session cookie. The session management module can then allow the user to re-join the session, assuming the login and authorization tokens are also valid.

Returning to block 520, the session management module also proceeds to block 524. At block 524, the user performs the desired actions on the page using the browser (e.g., managing patient health data). At block 526, the session management module determines whether the page has been unloaded (e.g., the browser window or tab has been closed by the user). If not, the session management module returns to block 524. If so, the session management module proceeds to block 528.

At block 528, the session management module stops the refresh timer discussed above at block 522. In an embodiment, this means that the session cookie will now expire at the set expiration time (e.g., 30 seconds later). At block 530, the session management module determines whether the user is logging out. If so, the session management module proceeds to block 532 and logs out the login token (as discussed in more detail above). If not, the flow ends.

Figure 6:
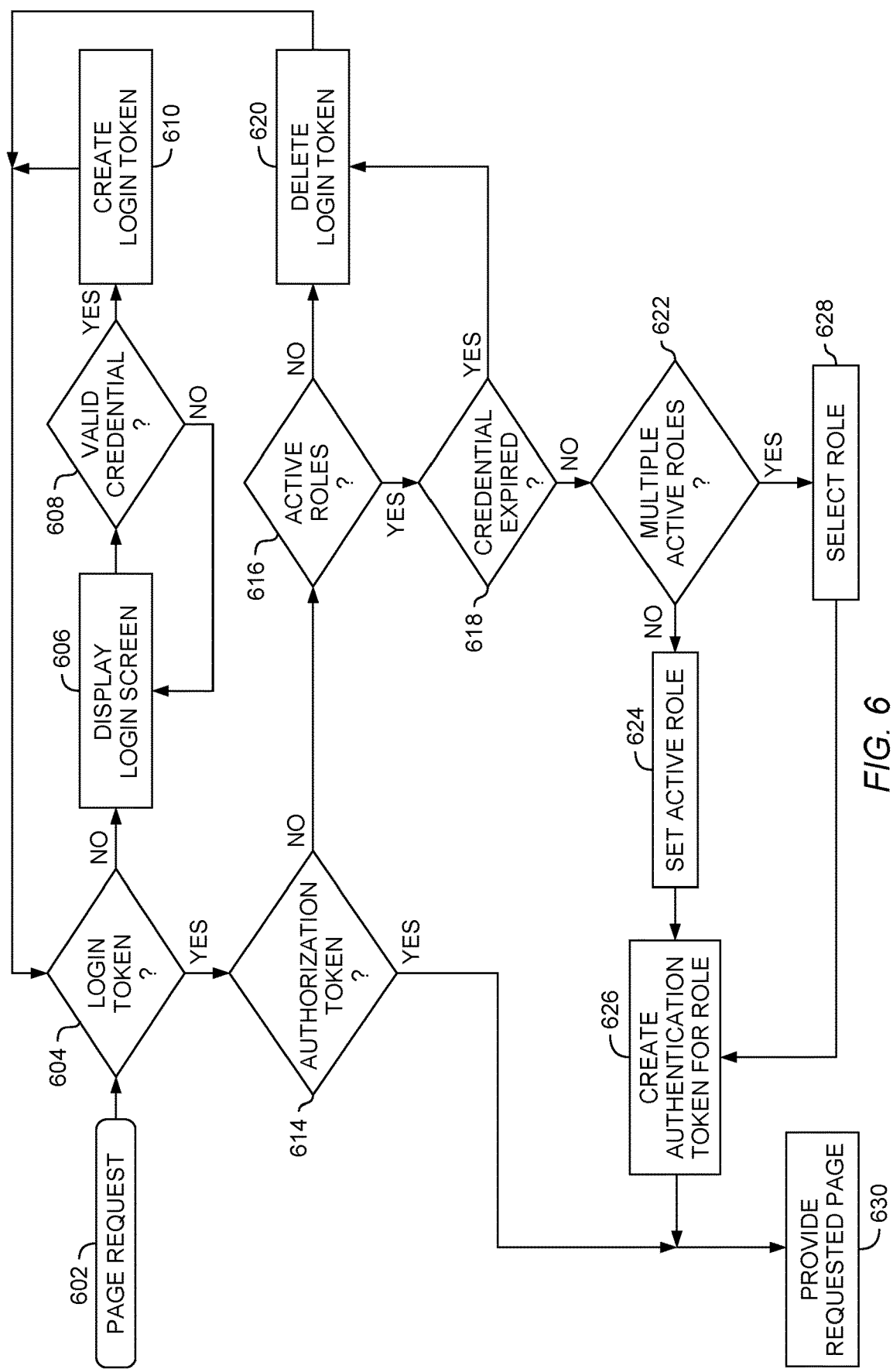
FIG. 6 is a flowchart illustrating client-side login token management with multiple roles, according to one embodiment described herein.

FIG. 6 is a flowchart illustrating client-side login token management with multiple roles, according to one embodiment described herein. In an embodiment, FIG. 6 illustrates handling multiple roles for a user in a system. At block 602, a client browser (e.g., the browser 122 illustrated in FIG. 4) receives a request to navigate to a page including an application (e.g., an application related to managing health data, as described above). At block 604, a session management module in the application (e.g., the session management module 424 illustrated in FIG. 4) determines whether the client system has a valid login token (e.g., the login token 426 illustrated in FIG. 4). If yes, the flow proceeds to block 614.

At block 614, the session management module determines whether the computing device has a valid authorization token (e.g., the authorization token 427 illustrated in FIG. 4). In an embodiment, a valid login token signifies that the computing device has logged in with valid credentials. Further, in an embodiment, a valid authorization token signifies that the client has selected a valid role for the desired page (e.g., care provider, patient, administrator, etc.). If the computing device has a valid authorization token, at block 614, the flow proceeds to block 630. At block 630 the browser provides the requested page to the user.

Returning to block 604, if the computing device does not have a valid login token, the flow proceeds to block 606. At block 606, the session management module directs the browser to display the login screen for the user.

At block 608, the session management module receives credentials from the user (e.g., a username and password, a fingerprint or other biometric scan, multi-factor authentication credentials, or other suitable credentials) and determines whether the credentials are valid. In an embodiment, this is done through communication with a care provider environment (e.g., the care provider environment 105 illustrated in FIG. 4) using a network (e.g., the network 405 illustrated in FIG. 4) and using known authentication techniques.

For example, a credential may have expired (e.g., a password may have expired). In an embodiment, the session management module can account for different credential expiration rules. For example, a care provider associated with a hospital may be required to change his or her password every 30 days, while a patient may only be required to change his or her password every 90 days. As another example, different roles may be associated with different institutions, and may have different credential expiration rules. For example, a given user may have a role as a care provider at two different hospitals. The first hospital may require password reset every 45 days, while the second hospital may require password reset every 60 days.

At block 608, the session management module determines whether the user's credential has expired for any of the roles associated with the user's credentials. In an embodiment, the session management module can retrieve this information from a care provider environment server (e.g., the care provider environment 105 illustrated in FIG. 1) using a data repository (e.g., the data repository 118 illustrated in FIG. 1). Alternatively, the session management module can retrieve this information from a third party location (e.g., a server or website) associated with the relevant role, or from another location. If the user's password has expired for any active role, the flow proceeds to block 606 and returns to the login screen.

At block 610, if the session management module determines that the credentials are valid, it creates a login token and stores it locally on the computing device. The session management module then returns to block 604 and checks for a valid login token. Returning to block 608, if the session management module determines that the credentials are not valid, it returns to block 606 and the login screen. In an embodiment, the session management module displays an error message and asks the user to re-enter his or her credentials on the login screen.

Returning to block 614, if the session management module determines that the computing device does not have a valid authorization token, the flow proceeds to block 616. At block 616 the session management module determines whether the user has any active roles. For example, the session management module can determine whether any active roles are associated with the user's credential. In an embodiment, the session management module can retrieve this information from a care provider environment server (e.g., the care provider environment 105 illustrated in FIG. 1) using a data repository (e.g., the data repository 118 illustrated in FIG. 1).

In an embodiment, a user can be associated with a variety of roles. For example, roles can include super user, customer service representative, institutional administrator, managing physician, prescribing physician, physician assistant, nurse, technician, device kitter (e.g., for medical devices), device distributor (e.g., for medical devices), patient, patient care giver (e.g., family member or guardian). These are merely examples of possible roles, and any suitable roles can be used. Further, in an embodiment, various institutions can rename or create their own roles with their own capabilities. This can be done through a user interface provided to the institution, or in any other suitable way.

If the user does not have any active roles, the flow proceeds to block 620. At block 620 the session management module deletes the login token and the flow proceeds to block 604, where the user will be required to login again.

Returning to block 616, if the session management module finds an active role associated with the user's credential, the flow proceeds to block 618. At block 618, the session management module determines whether the user's credential has expired. In an embodiment, a credential is associated with a time duration and will expire after that duration. In an embodiment, the time-out duration can vary across institutions and roles, and can be configured by a user. If the session management module determines that the credential has expired, the flow moves to block 620 where, as discussed above, the session management module deletes the login token and the flow proceeds to block 604.

Returning to block 618, if the user's credential has not expired, the flow proceeds to block 622. At block 622, the session management module determines whether the user has multiple active roles. If not, meaning the user has exactly one active role associated with his or her credentials, the flow proceeds to block 624 and the session management module sets the active role. At block 626, the session management module then creates an authorization token for the selected role, and stores the authorization token. The flow then proceeds to block 630, as discussed above.

Returning to block 622, if the user has multiple active roles, the flow proceeds to block 628. At block 628, the session management module selects a role (e.g., by allowing the user to select a desired role through a suitable user interface). In one embodiment, a user is associated with one selected role, of the available active roles. Alternatively, a user can be associated with multiple roles at the same time. This is discussed further with regard to FIG. 8, below. After role is selected, the flow proceeds to block 626. Block 626 is discussed further above.

Figure 7:
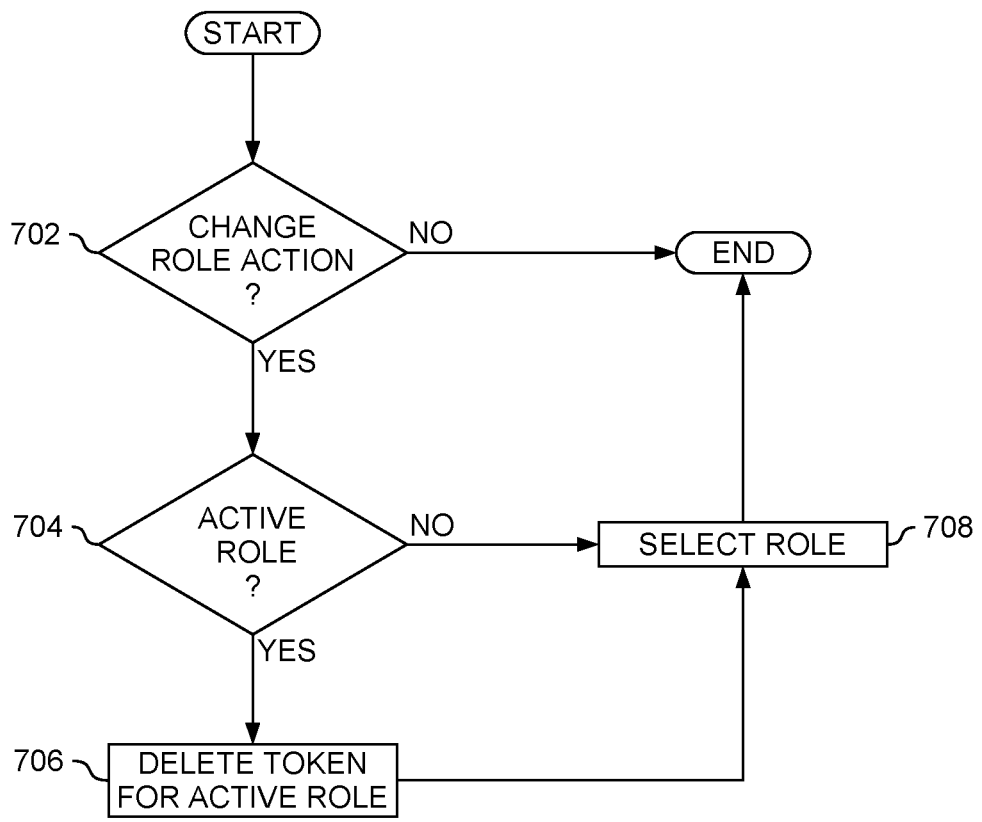
FIG. 7 is a flowchart illustrating changing roles, according to one embodiment described herein.

FIG. 7 is a flowchart illustrating changing roles, according to one embodiment described herein. In an embodiment, as discussed above, a user can be associated with multiple potential roles for a system (e.g., primary care provider, secondary care provider, observer, administrator, patient, patient guardian, patient assistant, etc.). In this embodiment, a user can change roles during a session. For example, a user can select a "change role" action using a drop-down, link, or other user interface technique. In an embodiment, this triggers a change role action.

At block 702 an application associated with a client browser (e.g., the browser 122 illustrated in FIG. 4) receives an action and determines whether it is a change role action. If not, the flow ends. If so, the flow proceeds to block 704. At block 704 a session management module in the application (e.g., the session management module 424 illustrated in FIG. 4) determines whether the user has a currently active role. If yes, the flow, proceeds to block 706. At block 706, the session management module deletes the token associated with the active role. The flow then proceeds to block 708. In an embodiment, the session management module follows this flow only if the user has more than one active role. In this embodiment, the session management module determines whether the user has only one active role and, if so, it does not allow the user to change roles. Alternatively, the session management module allows the user to select a new role even if the user has only one active role.

At block 708, the session management module selects a role. In an embodiment, this is similar to blocks 622-628 discussed above with regard to FIG. 6. For example, assuming the user has multiple active roles, the session management module displays a user interface (e.g., drop downs, radio buttons, or another suitable interface) to allow the user to select the active role. This is discussed further with regard to block 628 in FIG. 6 and with regard to FIG. 8. The session management module then creates a token for the role (e.g., as discussed above with regard to block 626 in FIG. 6). The flow then ends.

Figure 8:
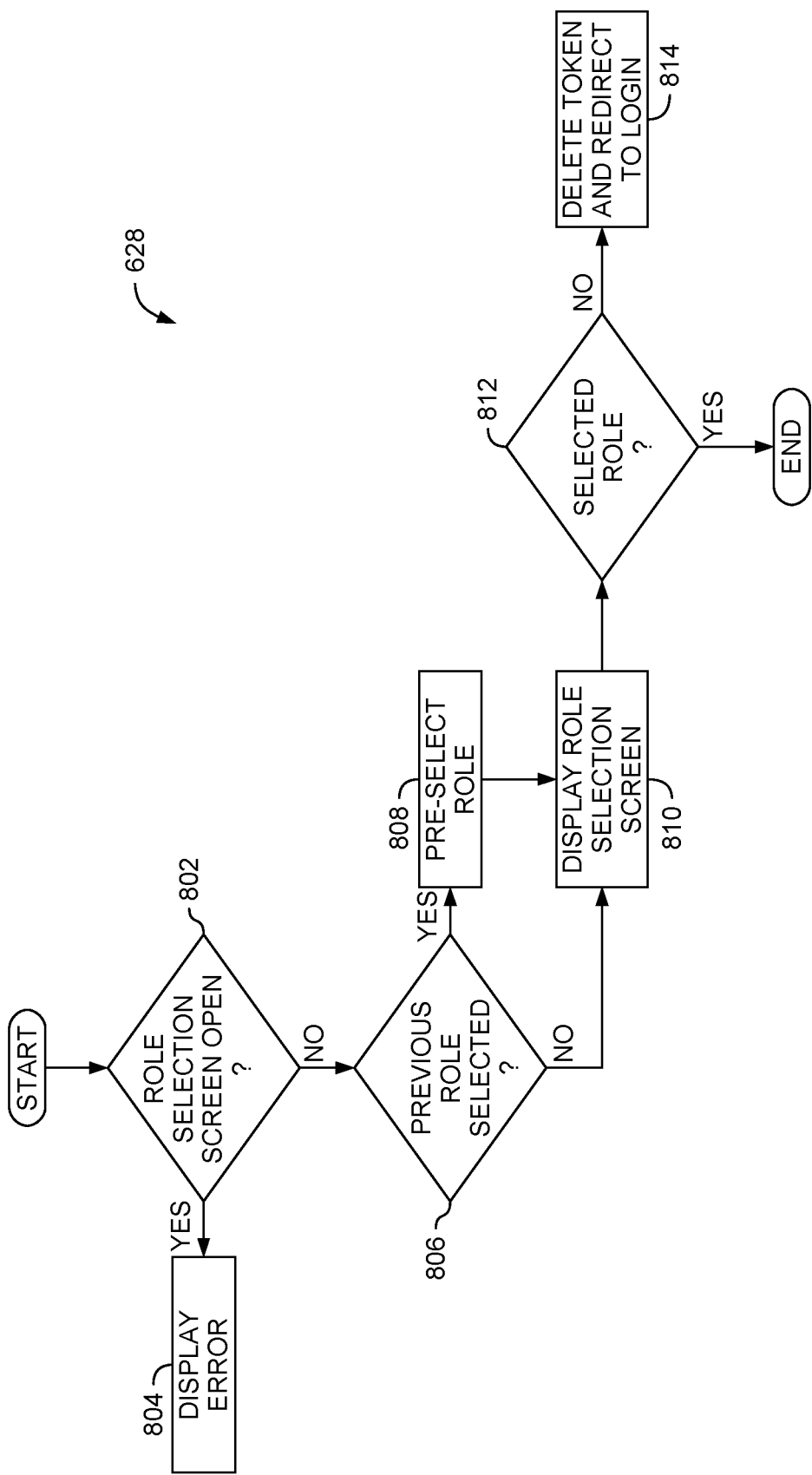
FIG. 8 is a flowchart illustrating user selection of roles, according to one embodiment described herein.

FIG. 8 is a flowchart illustrating user selection of roles, according to one embodiment described herein. In an embodiment, this Figure corresponds with block 628, discussed above with regard to FIG. 6. At block 802, an application associated with a client browser (e.g., the browser 122 illustrated in FIG. 4) determines whether a role selection screen is already open in the user's browser. In an embodiment, this can be done using a suitable cookie or token. For example, when the role selection screen is opened, the session management module can write a flag to a local cookie (e.g., the session cookie) indicating that the role selection screen is open. The session management module can then clear that flag when the role selection screen is closed. If yes, at block 804 the application displays an error to the user (e.g., notifying the user of the existing open window) and the flow ends. In an embodiment, the application can activate the currently open role selection window and bring it to the forefront to the user.

Returning to block 802, if the application does not find an open role selection screen, the flow proceeds to block 806. At block 806, a session management module in the application (e.g., the session management module 424 illustrated in FIG. 4) determines whether a previous role was selected. If yes, the flow proceeds to block 808. At block 808, the session management module pre-selects the previously selected role. In an embodiment, this is set as the default selection in the role selection user interface the previously selected role.

The flow then proceeds to block 810. At block 810, the application displays to the user a role selection screen. In embodiment, this includes a suitable user interface for the user to select a desired role (e.g., a drop-down, radio buttons, etc.). As discussed above, in one embodiment a user is associated with one role. In this embodiment, the user selects the desired role using the user interface. Alternatively, the user can be associated with multiple roles at the same time. In this embodiment, the user can select multiple roles, together, using the user interface.

At block 812, the session management module determines whether the user selected a role. If so, in one embodiment, the flow ends. Alternatively, if the user has selected a role, the session management module determines whether the current token remains valid. For example, the token can be set to expire after a given duration of time. If the user spends too long at the role selection screen, the current token may have timed out and may no longer be valid. If this is the case the flow proceeds to block 814. The flow also proceeds to block 814 if the user has not selected a role.

At block 814 the session management module deletes the current token and directs the user to the login screen (e.g., as discussed above with regard to FIGS. 5 and 6).

Figure 9:
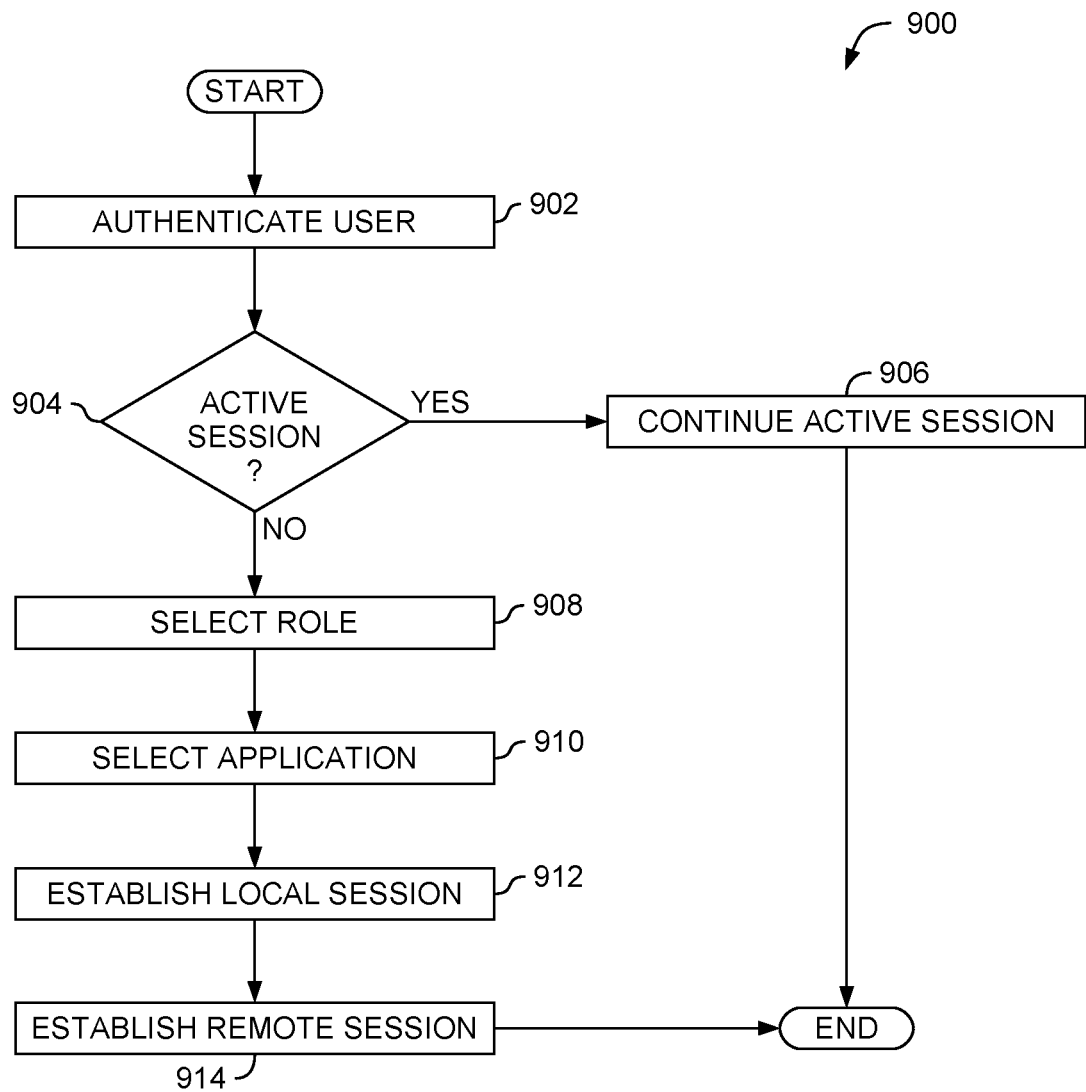
FIG. 9 is a flowchart further illustrating client-side login token management for multiple applications, according to one embodiment described herein.

FIG. 9 is a flowchart 900 further illustrating client-side login token management for multiple applications, according to one embodiment described herein. At block 902, a user is authenticated. For example, in an embodiment, a client browser (e.g., the browser 122 illustrated in FIG. 4) receives a request to navigate to a login page, and the user is authenticated using the login page. The authentication and login process is discussed further with regard to FIGS. 5 and 6, above.

At block 904, a session management module (e.g., the session management module 424 illustrated in FIG. 4) determines whether the user has an active session. In an embodiment, the session management module can do this by identifying an existing session cookie (e.g., the session cookie 428 illustrated in FIG. 4), as discussed further with regard to FIG. 5, above. For example, a user may have had an ongoing active session, but the user may have closed the browser window(s) associated with the session. The user may, however, still have an active session cookie (e.g., a session cookie that has not yet timed out). If so, the flow proceeds to block 906, and the user continues with the active session.

If the session management module does not identify an active session, the flow proceeds to block 908. At block 908, the session management module selects a role. In an embodiment, the techniques illustrated in FIG. 8 can be used select the role. At block 910, the session management module selects an application. In an embodiment, multiple applications can be associated with the same session management module. For example, a particular institution may have several different associated applications (e.g., a patient management application, a patient care management application, an administrative application, etc.). Alternatively, multiple different institutions (e.g., multiple different hospitals, care providers, medical device providers, etc.) may each have their own application associated with common credentials for a user. At block 910, the user selects the application for which the user wishes to proceed (e.g., using a suitable user interface). For example, the browser can display a user interface to allow the user to select an application (e.g., using a drop down, check boxes, radio buttons, or another suitable user interface).

The embodiment illustrated in FIG. 9 shows selection of an application (e.g., at block 910) after selection of a role (e.g., at block 908). In an embodiment, these blocks can be reversed. For example, a user could first be prompted to select an application. After selecting the application, the session management module could automatically select a role suitable for that application (e.g., the role in use by a different application, or a previously selected role). Further, the session management module could automatically select a role for the new application that is related to, but different from, a previously selected role. For example, a user may have the role of a primary care provider for the user's primary care facility. If the user logs in to an application related to a different care facility (e.g., a different hospital), the session management module could automatically select the role of secondary care provider, or observer.

At block 912, the session management module establishes a local session associated with the selected role and application. This is discussed further wither regard to FIGS. 5 and 6, above. For example, the session management module generates and maintains suitable local tokens and a suitable session cookie.

At block 914, the care provider environment (e.g., the care provider environment 105 illustrated in FIG. 4) establishes a remote session associated with the selected application and user. For example, the session management module can transmit a request through a communication network to a request processing component (e.g., the request processing component 440 illustrated in FIG. 4) associated with a server application (e.g., the server application 435 illustrated in FIG. 4). In an embodiment, this request includes the session cookie generated at the local system. The request processing component can initialize database information (e.g., in the database 460 illustrated in FIG. 4) and otherwise establish a remote session. For example, the request processing component can receive the session cookie and use it to establish a corresponding remote session on the server.

Figure 10:
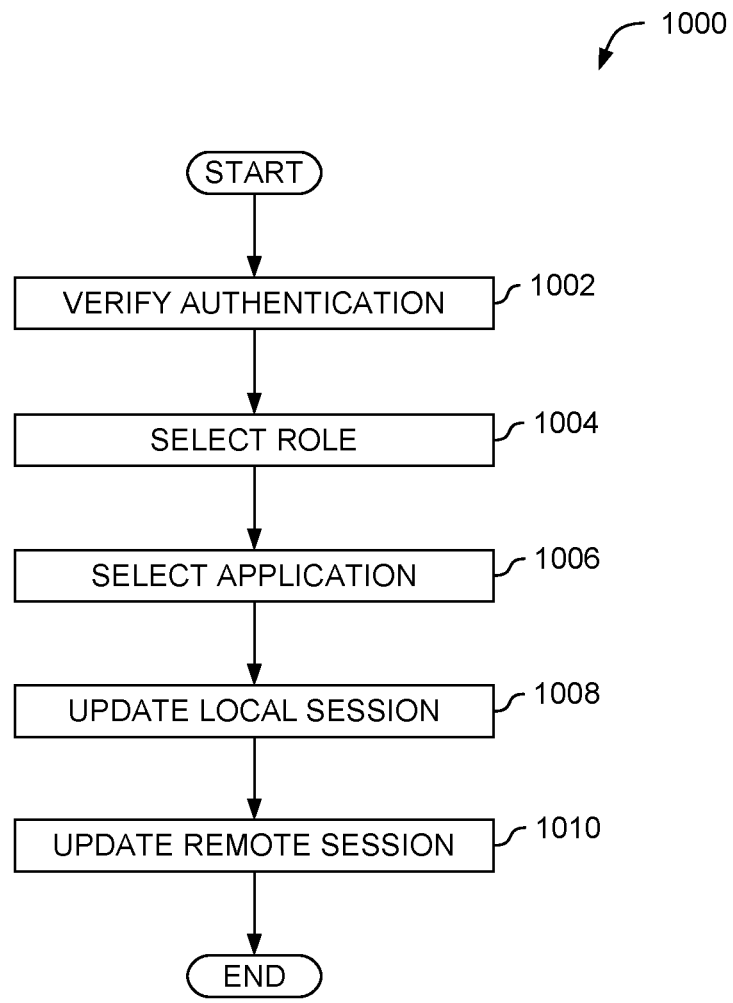
FIG. 10 is a flowchart further illustrating role selection for multiple applications, according to one embodiment described herein.

FIG. 10 is a flowchart 1000 further illustrating role selection for multiple applications, according to one embodiment described herein. In an embodiment, these techniques can be used to select a new role after local and remote sessions have been established. At block 1002, a session management module (e.g., the session management module 424 illustrated in FIG. 4) verifies that the user is authenticated. At block 1004, the session management module selects a role for the user. In an embodiment, the techniques illustrated in FIG. 8 can be used select the role.

At block 1006, the session management module selects an application. This is discussed further with regard to block 910 in FIG. 9, above. At block 1008, the session management module updates the local session information. In an embodiment, this includes updating the local tokens and session cookie, as discussed further with regard to FIGS. 5 and 6, above.

In one embodiment, the session management module ensures that each user is logged into one application at a time. If the user is already logged into one application, and seeks to login to another application, the session management module can take an appropriate action. For example, the session management module can log the user out of the prior application and log the user in to the new application. Alternatively, the session management module can display an error message to the user indicating that the user is already logged in to one application. Further, the session management module can allow the user to select whether to log out of the prior application. Alternatively, the session management module allows the user to log in to multiple applications. In an embodiment, the session cookie, or another suitable local token or cookie, can be used to track application usage by the local user.

At block 1010, the remote session is updated. For example, the session management module can transmit a request through a communication network to a request processing component (e.g., the request processing component 440 illustrated in FIG. 4) associated with a server application (e.g., the server application 435 illustrated in FIG. 4). The request processing component can then update session information, including database information (e.g., in the database 460 illustrated in FIG. 4) and other remote session information.

Figure 11:
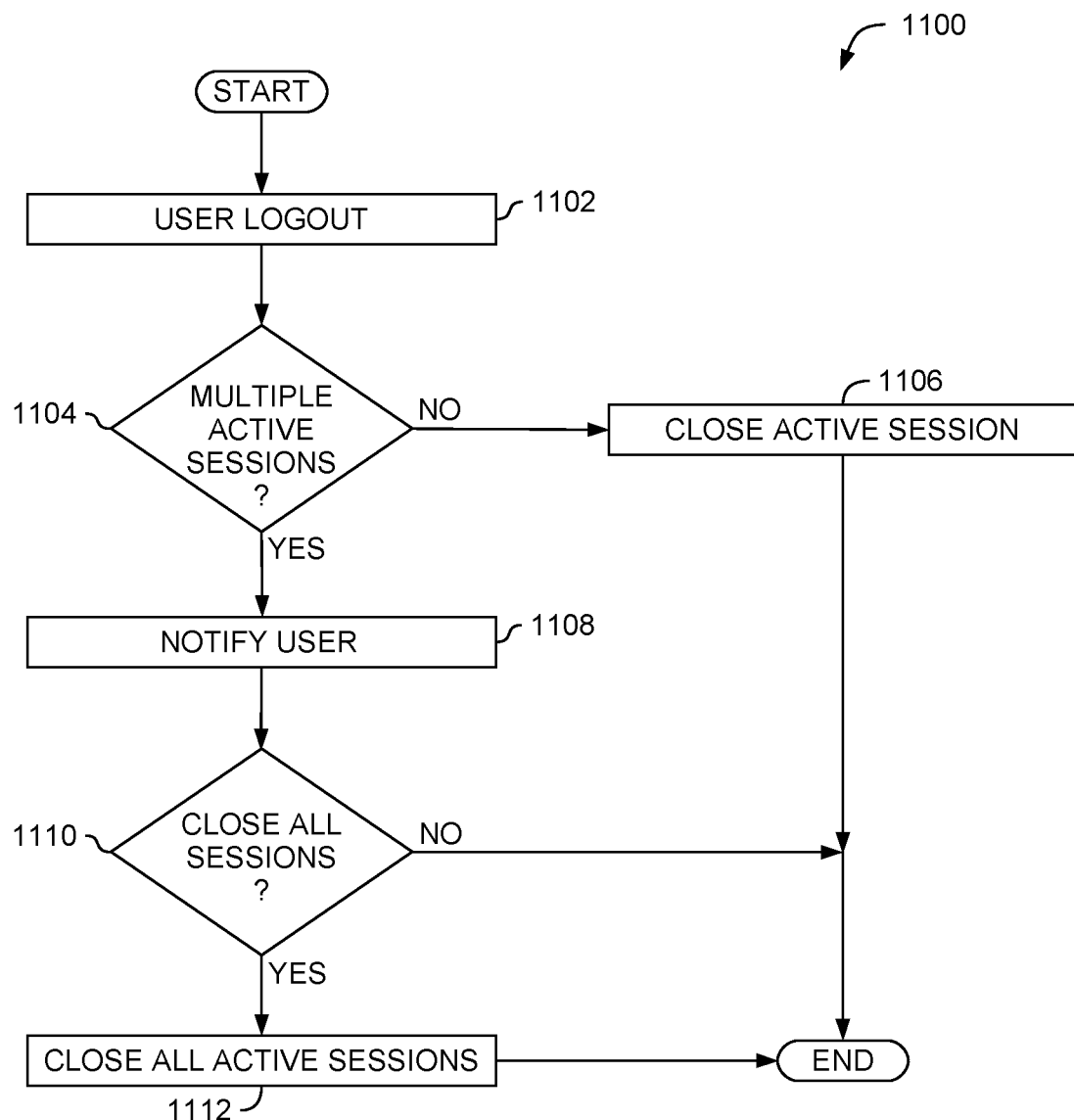
FIG. 11 is a flowchart further illustrating concluding a session using login token management, according to one embodiment described herein.

FIG. 11 is a flowchart 1100 further illustrating concluding a session using login token management, according to one embodiment described herein. At block 1102, a user logs out. For example, in an embodiment, a client browser (e.g., the browser 122 illustrated in FIG. 4) receives a request to navigate to a page including a logout screen. At block 1104, a session management module (e.g., the session management module 424 illustrated in FIG. 4) determines whether the user has multiple active local sessions. In an embodiment, the session management module uses a session cookie (e.g., the session cookie 428 illustrated in FIG. 4). For example, the session cookie can be used to track multiple active sessions (e.g., multiple applications) by including tracking data for each session in the cookie. Alternatively, multiple session cookies can be used to track multiple sessions.

At block 1106, if the user does not have multiple active sessions, the session management module closes the active session, logs out the user, and the flow ends. At block 1108, if the user has multiple active sessions, the session management module notifies the user. For example, the user can be provided with a user interface notifying the user of the multiple active sessions, and asking the user if the user wishes to close all active pending sessions. In an embodiment, the user may not be aware that multiple active sessions are pending (e.g., because the user may have multiple browser windows or tabs open).

At block 1110, the user decides whether to close all active sessions. If yes, the flow proceeds to block 1112 and the session management module closes all active sessions, logs out the user. Further, in an embodiment, the session management module removes the user history from the computer. For example, the session management module can remove any remaining tokens, cookies, etc. associated with the user. This acts as a security feature in case the user is active on a shared computer. Returning to block 1110, if the user does not close all active sessions, the active sessions continue on.

In the preceding, reference is made to embodiments presented in this disclosure. However, the scope of the present disclosure is not limited to specific described embodiments. Instead, any combination of the described features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s).

As will be appreciated by one skilled in the art, the embodiments disclosed herein may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium is any tangible medium that can contain, or store a program for use by or in connection with an instruction execution system, apparatus or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments presented in this disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In view of the foregoing, the scope of the present disclosure is determined by the claims that follow.

We claim:

1. A method comprising:
authenticating, at a remote computing device that comprises a user interface, a user for an application for viewing and classifying electrocardiogram (ECG) data and cardiac events;
in response to the authenticating, generating and maintaining a login token for the user at the remote computing device;
generating and maintaining an authorization token associated with a role of the user at the remote computing device;
requesting a page of the application via the user interface, the page comprising the ECG data and a list of the cardiac events;
determining, using the authorization token, that the user is authorized to access the page; and
accessing the page, via the user interface, in response to the determining.

2. The method of claim 1, further comprising:
after the accessing the page, reclassifying at least one of the cardiac events from a first classification to a second classification using the user interface.

3. The method of claim 2, wherein the first classification is one of an atrioventricular block event or a ventricular trigeminy event, wherein the second classification is the other of the atrioventricular block event or the ventricular trigeminy event.

4. The method of claim 1, wherein the login token is encrypted.

5. The method of claim 4, wherein the authorization token is encrypted.

6. The method of claim 1, wherein the remote computing device is a mobile phone, wherein the application is a native application on the mobile phone.

7. The method of claim 6, wherein the accessing comprises accessing the ECG data and the cardiac events previously processed by a server physically separate from the remote computing device.

8. The method of claim 1, wherein the application is a browser.

9. The method of claim 1, wherein the login token and the authorization token are stored on the remote computing device.

10. The method of claim 1, wherein the determining that the user is authorized to access the page is accomplished without interaction with a server.

11. A non-transitory computer-readable medium containing computer program code that, when executed by one or more computer processors, performs an operation at a remote computing device, the operation comprising:
authenticating a user for an application for viewing and classifying electrocardiogram (ECG) data and cardiac events;
in response to the authenticating, generating and maintaining a login token for the user;
generating and maintaining an authorization token associated with a role of the user;
in response to a request to access a page of the application via a user interface, determining—using the authorization token—that the user is authorized to access the page, wherein the page comprises the ECG data and a list of the cardiac events; and
accessing the page, via the user interface, in response to the determining.

12. The non-transitory computer-readable medium of claim 11, the operation further comprising:
after the accessing the page, reclassifying at least one of the cardiac events from a first classification to a second classification in response to a command entered via the user interface.

13. The non-transitory computer-readable medium of claim 12, wherein the first classification is one of an atrioventricular block event or a ventricular trigeminy event, wherein the second classification is the other of the atrioventricular block event or the ventricular trigeminy event.

14. The non-transitory computer-readable medium of claim 11, wherein the login token is encrypted.

15. The non-transitory computer-readable medium of claim 11, wherein the authorization token is encrypted.

16. The non-transitory computer-readable medium of claim 11, wherein the remote computing device is a mobile phone, wherein the application is a native application on the mobile phone.

17. The non-transitory computer-readable medium of claim 16, wherein the accessing comprises accessing the ECG data and the cardiac events previously processed by a server physically separate from the remote computing device.

18. The non-transitory computer-readable medium of claim 11, wherein the application is a browser.

19. The non-transitory computer-readable medium of claim 11, wherein the login token and the authorization token are stored on the remote computing device.

20. The non-transitory computer-readable medium of claim 11, wherein the determining that the user is authorized to access the page is accomplished without interaction with a server.

* * * * *